United States Patent [19]

Neas et al.

[11] Patent Number: 4,882,286
[45] Date of Patent: Nov. 21, 1989

[54] DIGESTION APPARATUS USEFUL FOR A KJELDAHL METHOD

[75] Inventors: Edwin D. Neas, Indian Trail, N.C.; Terry S. Floyd, Clover, S.C.

[73] Assignee: CEM Corporation, Matthews, N.C.

[21] Appl. No.: 104,569

[22] Filed: Oct. 2, 1987

Related U.S. Application Data

[63] Continuation of Ser. No. 874,278, Jun. 13, 1986, abandoned.

[51] Int. Cl.⁴ .............................................. G01N 1/00
[52] U.S. Cl. ..................................... 436/175; 422/78; 422/79; 422/80; 422/102; 422/103; 422/104; 219/10.55 R; 219/10.55 A; 219/10.55 D; 250/455.1; 34/1
[58] Field of Search .................. 436/175; 422/78, 79, 422/80, 102, 103, 104; 250/455.1; 219/10.55 R, 10.55 A, 10.55 D; 34/1

[56] References Cited

U.S. PATENT DOCUMENTS

| | | | |
|---|---|---|---|
| 2,868,626 | 1/1959 | Allen | 422/68 |
| 2,932,558 | 4/1960 | Bennet | 422/78 |
| 3,437,211 | 4/1969 | Lindsey | 422/101 |
| 3,963,420 | 6/1976 | Matsumoto et al. | 436/175 |
| 4,080,168 | 3/1978 | Abu-Samra et al. | 422/68 |
| 4,307,277 | 12/1981 | Maeda et al. | 219/10.55 R |
| 4,315,573 | 2/1982 | Bradley et al. | 427/386 |
| 4,347,216 | 8/1982 | Kawasaki et al. | 422/78 |
| 4,363,639 | 3/1981 | Gladon | 55/95 |
| 4,364,753 | 12/1982 | Wagner | 55/179 |
| 4,490,287 | 12/1984 | Hardwick et al. | 219/10.55 R |
| 4,681,740 | 7/1987 | Commarmot et al. | 422/78 |

FOREIGN PATENT DOCUMENTS

| | | | |
|---|---|---|---|
| 1045341 | 11/1953 | France | 422/103 |
| 1385483 | 2/1975 | United Kingdom | 422/102 |

OTHER PUBLICATIONS

P. Barrett et al, *Analytical Chemistry*, 7, 1021 (1978), Prolabo Literature.
Bradstreet, *The Kjeldahl Method for Organic Nitrogen*, 1965, pp. 40–42.
Kjel-Foss Automatic Literature by A/S N. Foss Electric.
S. Brayton of the Hach Company, "A Practical Kjeldahl-Nitrogen Method".

*Primary Examiner*—Barry S. Richman
*Assistant Examiner*—Lynn M. Kummert
*Attorney, Agent, or Firm*—Timothy R. Kroboth

[57] ABSTRACT

A microwave-based apparatus for rapid digestion of a sampel by a Kjeldahl method is provided which includes a reaction vessel surrounded by an insulator in the form of, for example, a cup. The reaction vessel is disposed in the internal chamber of a microwave system, which includes a wall having an aperture. A connector tube is slidably disposed in the aperture, wherein one end of the tube is connected to the mouth of the reaction vessel, and the other end is connected to a suction device external to the chamber. A biasing element is provided outside the chamber to assist in joining the slidable connector tube to the mouth of the vessel, yet enabling removal of the vessel from the chamber without detachment of the biasing element.

10 Claims, 3 Drawing Sheets

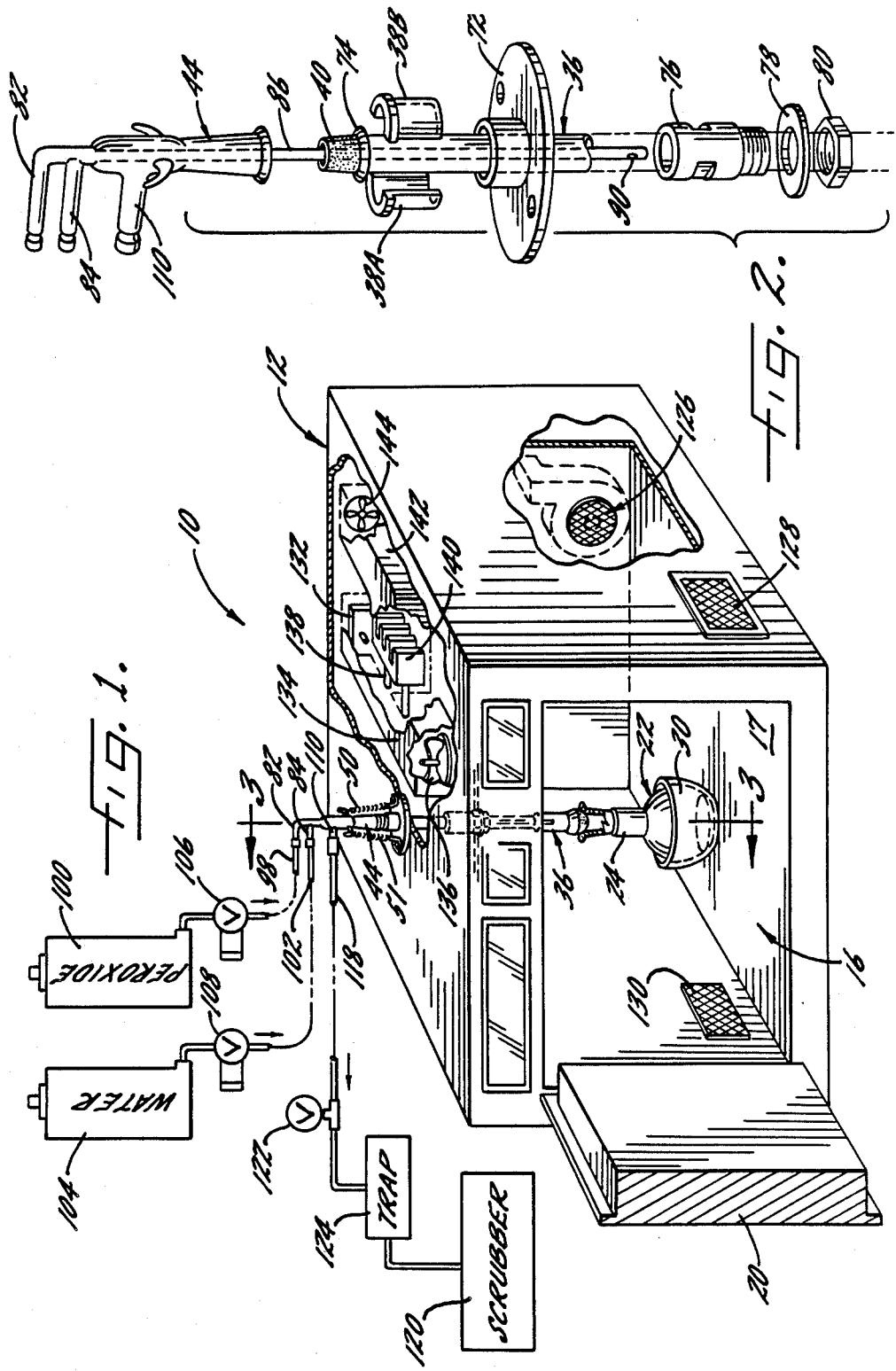

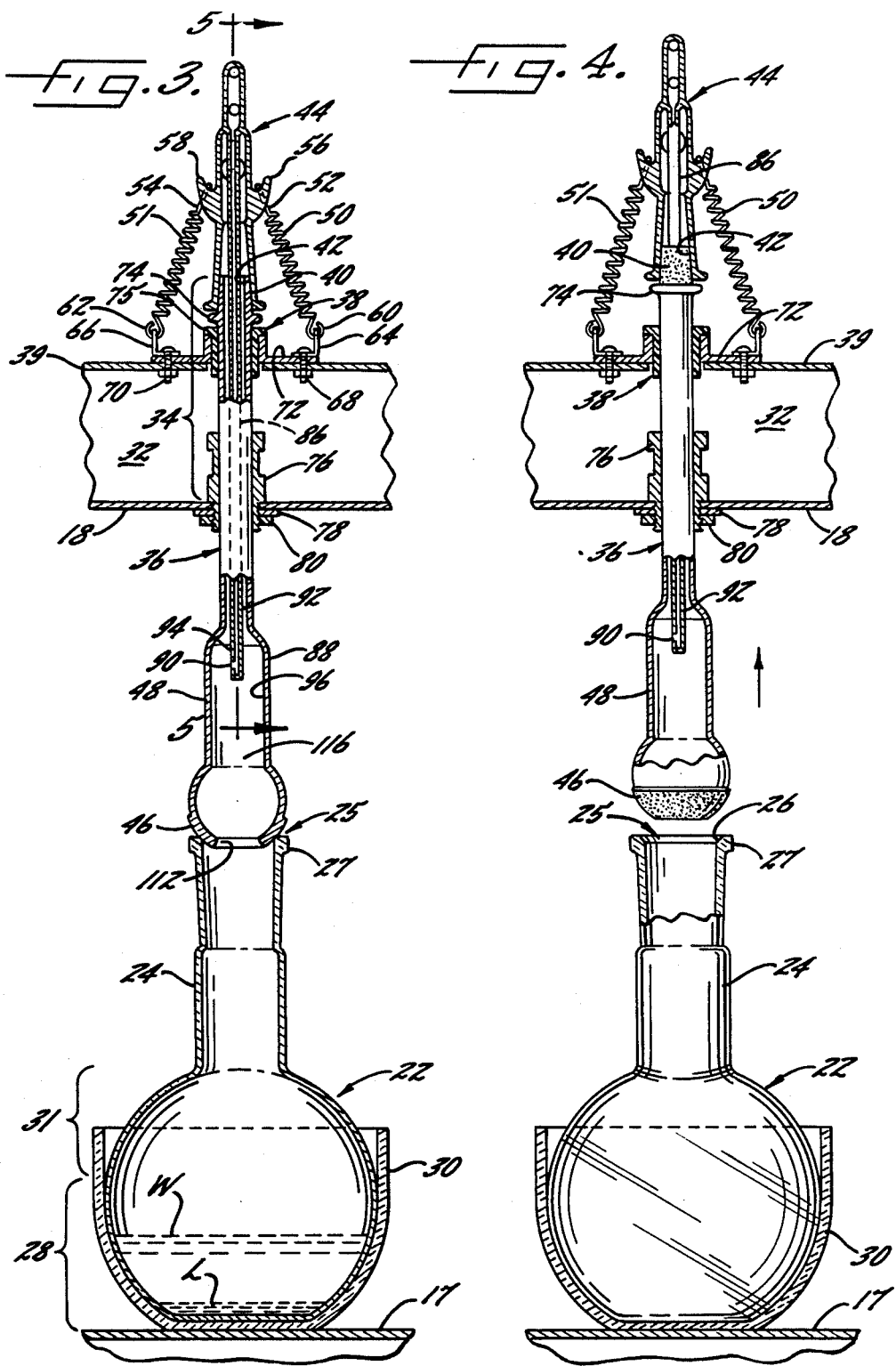

DIGESTION APPARATUS USEFUL FOR A KJELDAHL METHOD

This application is a continuation of application Ser. No. 874,278 filed June 13, 1986, now abandoned.

Technical Field

The present invention relates to a microwave-based apparatus for rapid digestion, and to a rapid Kjeldahl digestion method.

BACKGROUND ART

A problem with wet digestion of organic samples, particularly a gas-generating, tissue digestion such as the Kjeldahl digestion, is boil-over with resultant loss of sample, due to excessive foaming and/or bumping. Further problems are safe disposal of off gases including the corrosive fumes of an acid digesting agent, loss of acid values during digestion, and, for a Kjeldahl digestion especially, length of digestion time.

In recent years, as illustrated by U.S. Pat. No. 4,080,168 to Abu-Samra et al, U.S. Pat. No. 4,347,216 to Kawasaki et al, P. Barrett et al., *Analytical Chemistry*, 7, 1021 (1978), and a microwave digester made by Prolabo, interest has focused on microwave oven-based, wet digestion. However, the problems of boil-over, safe disposal of off gases, and loss of acid values have remained.

For instance, Abu-Samra et al, while stating that bumping and frothing are virtually eliminated, advise that it may be desirable to incorporate an interrupted duty cycle type of timer to prevent sample boil-over. Kawasaki et al remove off gases through a hollow gas collector connected to an external scrubber and removably mounted, sample decomposing containers; and include an exhaust fan in the microwave oven thereof. However, Kawasaki et al describe a complex equation for selecting an irradiation time and an irradiation interruption period, to control foaming and bumping at an early stage of digestion.

Noting several shortcomings of Abu-Samra et al's fume removal apparatus including deterioration of the interior Plexiglas box, Barrett et al describe a round bottom flask with a ground glass joint connected directly to an exit port which is coupled to an aspirator. However, a ground glass joint in the proximity of a hot, bubbling liquid that may leak into the joint, has a tendency to freeze.

Prolabo's microwave digester vents gases through a container lid connected to a scrubber via a side arm.

As illustrated by R. B. Bradstreet, *The Kjeldahl Method for Organic Nitrogen*, Academic Press, N.Y., 1965, pp. 40–42, and a Kjeldahl technique of A/S N. Foss Electric, hydrogen peroxide is useful as an additive for reducing boil-over. In the Foss Kjeldahl method, a protein sample is mixed with conventional Kjeldahl digestion ingredients, viz., 10–15 ml concentrated sulfuric acid, 0.75 g mercuric oxide catalyst and 15 g potassium sulfate; 10 ml hydrogen peroxide (35%) is combined with the mixture; the mixture is heated using a high flame; the mixture is heated with a low flame; and 110 ml deionized water is added to the digestate, while cooling the reaction vessel using a blower. Although fast compared to other Kjeldahl methods, this method nevertheless requires twelve minutes to produce a digested sample. The method uses a 0.5 sample when protein content is more than 45%, and a 1.0 g sample when protein content is less than 45%. The apparatus used in the method includes a scrubber connected to a side tube of the reaction vessel.

Also known, as exemplified by a publication authored by S. Brayton of the Hach Company and entitled "A Practical Kjeldahl-Nitrogen Method", is a sulfuric acid-stabilized, hydrogen peroxide prepared by mixing 1 part of concentrated sulfuric acid with 4 parts of 50% hydrogen peroxide. As illustrated by U.S. Pat. No. 3,437,211 to Lindsey and U.S. Pat. No. 4,363,639 to Gladon, a connector tube having coaxial inlet/outlet passageways is known, and as exemplified by U.S. Pat. No. 3,963,420 to Matsumoto et al sample-dissolving apparatus including a condenser, is known.

Considering the foregoing, it can be understood that there is a need for an improved microwave-based, digestion apparatus. Furthermore, there is a need for a rapid Kjeldahl digestion method, that is, a method that yields a digestate in less than about ten minutes.

DISCLOSURE OF THE INVENTION

It is accordingly an object of the present invention to provide an improved microwave-based, digestion apparatus.

It is a further object of the present invention to provide a rapid Kjeldahl digestion method.

Additional objects, advantages and novel features of the present invention are set forth in the description that follows, and in part will become apparent to those skilled in the art upon examination of the following description or may be learned by practice of the invention.

To achieve the foregoing objects and in accordance with the purpose of the present invention, as embodied and broadly described herein, there is provided a microwave-based apparatus for rapid digestion of a sample. The apparatus includes a microwave system having a wall with an aperture formed therethrough. Disposed within the microwave system is a reaction vessel, a portion of which is surrounded by a vessel contour-conforming, microwave-transparent insulator. Extending through the wall aperture is a connector tube that is in an air-tight sealing relationship with the reaction vessel. Connected to an end of the connector tube exterior to the microwave system, is a scrubber.

Also provided by the present invention is a rapid Kjeldahl digestion method. In the method, there is placed within a microwave system a reaction vessel containing a protein sample to be digested, and a sufficient amount of Kjeldahl digestion ingredients suitable for effecting digestion. The reaction vessel is insulated by a microwave-transparent insulator. Sufficient microwave energy is applied to the contents of the reaction vessel to quickly attain an optimum Kjeldahl digestion temperature. Once the optimum temperature has been reached, sufficient microwave energy is applied to the vessel contents to maintain the optimum temperature until digestion is completed. During the second stage of heating, off gases are removed from the reaction vessel. Thereafter, the application of microwave energy is discontinued, and, while continuing to remove off gases, the digestate is diluted with water.

BRIEF DESCRIPTION OF THE DRAWING

Reference is now made to the accompanying drawing, which forms a part of the specification of the present invention, and which depicts a preferred embodiment of a digestion apparatus in accordance with the present invention.

FIG. 1 is a perspective, diagrammatic view of a preferred embodiment of a microwave-based, digestion apparatus in accordance with the present invention, with portions broken away;

FIG. 2 is an exploded, perspective view of a portion of the apparatus of FIG. 1;

FIG. 3 is an enlarged section taken along the line 3—3 in FIG. 1;

FIG. 4 is a view similar to FIG. 3, with connector tube 36 in raised position.

BEST MODE FOR CARRYING OUT THE INVENTION

Figure 5:
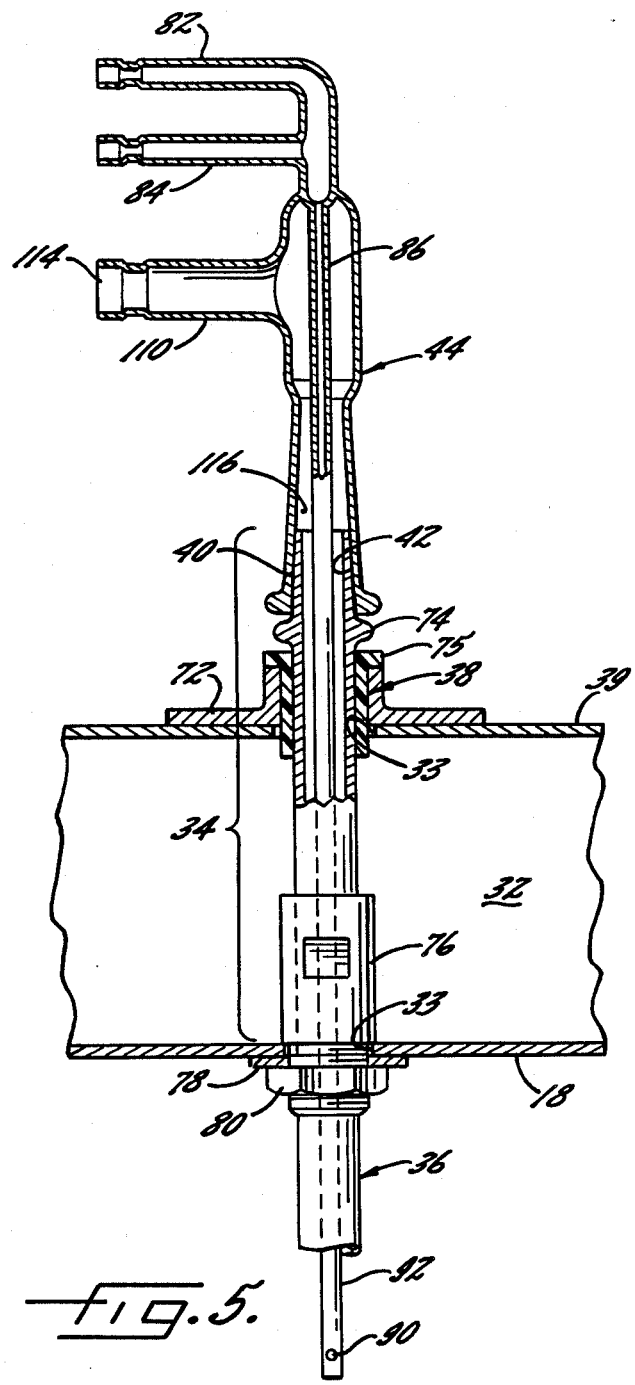
FIG. 5 is an enlarged section taken along the line 5—5 in FIG. 3.

As explained earlier, the present invention is directed to a microwave-based apparatus for rapid digestion, and to a rapid Kjeldahl digestion method using the apparatus. In the following description, the terms "upper", "lower", "top", "upward" and "downwardly" are intended to designate relative orientation as shown in the drawing.

FIG. 1 depicts a preferred microwave-based, digestion apparatus 10 in accordance with the present invention. Apparatus 10 includes a microwave system 12 including an internal chamber 16 formed in part by a floor 17, a chamber ceiling 18, shown in FIG. 3, and a door 20. The inner surface of each wall forming the internal chamber is preferably corrosion resistant, for example, coated with a fluorocarbon resin such as Teflon ®.

Disposed in internal chamber 16 is a reaction vessel 22 having a neck 24 that terminates in an inwardly tapered mouth 26, shown best in FIG. 4. Mouth 25 has an inside wall 26 and an outside wall 27. It is preferred for the reaction vessel to be made of quartz glass. Advantageously, neck 24 ends in the inwardly ground mouth of a 29/42 ground glass joint, as a joint of this diameter enables a microslide cover glass bearing a sample, to be dropped into vessel 22. A flat bottom, boiling flask is a preferred reaction vessel.

Referring to FIG. 3, a lower portion 28 of the rounded part of the vessel is insulated by a cup 30. The cup is molded to conform to the contour of the lower portion of the vessel, and is made of a microwave-transparent insulator. The insulator is a moldable material able to withstand temperatures up to about 500° C. such as glass fiber. When the cup is formed of glass fiber, an upper region of the cup may be hand molded after the vessel has been inserted into the cup, so that the cup is completely conformed to the vessel contour. If desired, insulation may be provided around an upper portion 31 of the rounded part of the vessel, thereby insulating the entire vessel except for neck 24. A suitable glass fiber cup has a thickness of about 4.5 mm+/−1 mm.

Microwave system 12 has a top wall 32, with an aperture 33 (shown in FIG. 5), advantageously having a diameter of about one-half inch, formed therethrough. An upper end 34 of a connector tube 36 extends through the aperture and protrudes above the top wall. A split bushing 38, suitably made of a heat-resistant material such as Telfon ®, effects a snug fit between the connector tube and an exterior panel 39 of the top wall. As shown in FIG. 2, bushing 38 splits into two pieces 38A and 38B for assembly. Exterior to the top wall is a male joint 40 of upper end 34, which forms an air-tight friction seal with a female joint 42 of an input/output tree 44. Preferably, tube 36 and tree 44 are made of glass, and joints 40,42 are tapered, ground glass joints.

With particular reference to FIG. 3, connector tube 36 has a rounded joint 46, preferably ground glass, at a bell-shaped, lower end 48 that is downwardly biased by springs 50,51 to form an air-tight seal with inwardly tapered mouth 25 (shown in FIG. 4) of the reaction vessel. The angle of inward taper of mouth 25 is adapted for sealingly mating with rounded joint 46. Preferably, the angle of taper is about 45°.

The rounded shape of joint 46 prevents freezing of the connector tube/reaction vessel juncture, which may occur if joint 46 is provided with a conventional tapered shape. The rounded shape also makes it easy for an operator to sealingly mate vessel mouth 25 with the connector tube.

Referring again to FIG. 3, upper spring ends 52,54 are attached to tree arms 56,58, respectively, and lower spring ends 60,62 attach to spring anchor clips 64,66, respectively. Screws 68,70 anchor the clips and a mounting bracket 72 to exterior panel 39. Mounting bracket 72 holds split bushing 38 in place. A connector tube shoulder 74 below male joint 40 seats on a flange 75 of bushing 38 to limit the downwardly biased movement of the connector tube.

As shown in FIG. 4, spring biasing of the connector tube/reaction vessel juncture permits upward movement of rounded joint 46, for ease of forming the air tight seal upon introducing vessel 22 into internal chamber 16, and for ease of removing the vessel when digestion is complete.

With reference again to FIG. 3, RF stub 76 provides a radiation-tight seal between connector tube 36 and chamber ceiling 18. Stub 76 is secured to ceiling 18 by a washer 78 and a nut 80.

As shown in FIGS. 2 and 5, tree 44 includes a pair of input tubes 82,84 that combine to form an inlet tube 86 that extends through connector tube 36. Inlet tube 86 is coaxially disposed within the connector tube.

Referring to FIG. 3, inlet tube 86 terminates in an upper part 88 of bell-shaped, lower end 48 of the connecting tube. An aperture 90 in the delivery end 92 of the inlet tube is disposed in an inlet tube side wall 94 so as to direct fluid flow against an inner wall surface 96 of bell-shaped, lower end 48. Alternatively, inlet tube 92 could have an open lower end.

With reference to FIG. 1, attached to input tube 82 is a section 98 of tubing that connects to a reservoir 100 containing, for example, aqueous hydrogen peroxide, and there is attached to input tube 84 a section 102 of tubing that connects to a reservoir 104 containing, for instance, water. The input lines from the reservoirs are regulated by one-way valves/solenoids 106,108, respectively.

Tree 44 further includes a gas outlet tube 110. As shown in FIG. 3, extending from an opening 112 in rounded joint 46 of the connector tube to an outlet tube mouth 114 (shown in FIG. 5) is a passageway 116, through which off gases escape from the reaction vessel.

With reference again to FIG. 1, attached to the gas outlet tube is a section 118 of tubing that connects to a scrubber 120 via a valve 122 that opens to the ambient atmosphere, and a trap 124. Polyethylene tubing is useful for tubing sections 98,102. However, tubing section 118 should be of a heat-resistant material such as Teflon ®, up to valve 122.

Microwave system 12 includes a corrosion resistant blower 126 and air intake panels 128,130 for flow of air through internal chamber 16. The blower is capable of providing high volume air flow through the chamber. By "high volume air flow" is meant on the order of 100 scfm or higher.

Microwave system 12 further includes a magnetron 132, a wave guide 134 and a radiation mixer 136. Between internal chamber 16 and the magnetron, a radiation isolator 138 is advantageously located in the wave guide, for absorbing excess reflected radiation to prevent damaging reflection back to the magnetron. The isolator includes magnetic shapes coupled with heat sinks. The isolator permits originating microwaves emitted from the magnetron to pass through unaffected, but absorbs reflected waves. The isolator has a propensity for attracting reflected radiation and thus will tend to draw reflected radiation out of the internal chamber.

The isolator converts the reflected radiation to heat, which is dissipated through an isolator heat exchanger 140. A heat exchanger duct 142 communicates with the heat exchanger and a fan 144, which draws off the produced heat. The fan and the isolator are able to absorb the full capacity of reflected energy for a zero load, for prolonged, indefinite operation.

The novel microwave-based, digestion apparatus of the present invention is used in a unique Kjeldahl digestion method as now described. The amounts of the various ingredients and the particular times included in the below description, are for a 0.5 g protein sample containing 45% or more protein. Twice as large a protein sample is used when the sample includes less than 45% protein.

The protein sample, preferably either a 0.5 g or 1.0 g sample depending upon the % protein, is added to reaction vessel 22, with conventional Kjeldahl digestion ingredients, to wit, about 10-15 ml of concentrated sulfuric acid, about 0.75 g of mercuric oxide, and about 15 g of potassium sulfate.

The insulated vessel is placed in internal chamber 16 of microwave system 12, which has a power output of 730 watts, an air-tight seal is formed between the vessel and the connector tube, and the microwave door is closed. In addition to providing for liquid input and gas output, as described below, the vertically disposed connector tube reduces the boil-over problem.

Preferably, a boil-over reducing additive, such as aqueous hydrogen peroxide solution, is added to the reaction vessel, advantageously with scrubber 120 turned on due to resultant fuming and heat generation. The additive is injected through inlet tube 86 into the reaction vessel in an amount sufficient to reduce boil-over.

About 2.5 ml of an about 40-50% hydrogen peroxide solution may be employed. Compared to 10 ml of 30% hydrogen peroxide, 2.5 ml of 50% hydrogen peroxide, which contains relatively less hydrogen peroxide and, of course, is a smaller volume of liquid, interestingly yields a relatively higher and more accurate protein number. A highly preferred 40% hydrogen peroxide solution is sulfuric acid-stabilized, and is prepared by mixing 1 part of concentrated sulfuric acid with 4 parts of 50% hydrogen peroxide. Hydrogen peroxide may assist rapid digestion.

After the boil-over reducing additive has been introduced into vessel 22, a digestion step may be immediately begun by the application of microwave energy to the vessel contents. In a first stage of the digestion step, the vessel contents are heated to quickly attain an optimum digestion temperature generally ranging from about 375° to 410° C. Gas generation with resultant foaming and/or bumping, characterizes this heating stage. Overshooting the optimum temperature results in an erroneously lower protein number.

Typically, the optimum temperature is quickly reached by using a 100% power output for approximately 1.5-1.75 minutes. By comparison, if insulator 30 were absent, minutes would be added to this stage of the digestion step due to heat loss through the reaction vessel walls. Furthermore, without insulator 30, the number of samples that can be simultaneously digested is power limited.

In a second heating stage, the power output is adjusted to maintain the optimum digestion temperature until digestion is complete. This step is typically accomplished by heating the vessel contents using 70% power for about 2.5 minutes.

For safety reasons, it is preferred for blower 126 to be on at all times during the novel method of the present invention. In addition to serving a safety function, the blower provides a cooling effect as air passes over the uninsulated upper portion of the reaction vessel, and over the part of the connector tube within internal chamber 16. As a result, the blower reduces the loss of acid, as off gases of the digestion step are cooled to cause acid condensation and return of condensed acid to the reaction vessel. It will be appreciated that this advantage may be fully realized even if the blower is not turned on until the beginning of the digestion step, and may achieved to a lesser extent if the blower is not turned on until the beginning of the second heating stage.

It will also be understood that the connector tube functions to reduce acid loss. Moreover, selection of a 500 ml size for the reaction vessel assists the reduction in loss of acid. Following the preferred aspects of the described method, vessel contents L in FIG. 3 represent the contents level in a 500 ml reaction vessel prior to beginning the digestion step.

After the digestion step is completed, the application of microwave energy is discontinued, and a dilution step may be immediately commenced. In this step, water is injected into the reaction vessel via the water input line through inlet tube 86. Mixing of the water with the hot digestate quickly results in the evolution of a large volume of gas. However, in a short time, cooling produced by the water, creates a negative pressure within the reaction vessel.

About 90 ml of water produces a desired final volume of about 100 ml. This volume of water, about 2.5 ml of peroxide, and about 10 ml of concentrated sulfuric acid represent minimum volumes, and as such are highly preferred, particularly since a relatively greater liquid volume in the digestion step results in a relatively longer time to reach the optimum temperature, the power output being constant.

FIG. 3 represents the contents level in a 500 ml reaction vessel after the dilution step. It is intended that the insulator cover the vessel to above this level.

To be able to immediately begin the dilution step, that is, to avoid an intervening cooling step, a pulsed addition of water is preferably employed. A highly preferred pulsing technique involves intermittently opening and closing the water input line until sufficient water has been added that there is a controlled gas evolution, that is, a gas evolution that does not cause a mechanical bumping in which the connector tube/reaction vessel joint momentarily opens and closes as a result of which off gas escapes through the joint. About seventy pulses in each of which the water line is open for about 0.3 seconds and closed for about 0.65 seconds, with the water line being open thereafter for about 40 seconds, has been found adequate.

If pulsed addition will not be used during the dilution step, a cooling step should be used to control the sudden surge in gas evolution. A cooldown period of from about 20 seconds to one minute is useful. However, a large, sudden evolution of gas may cause mechanical bumping. It will be understood that a cooldown period of about several minutes or longer could be employed to minimize the likelihood of mechanical bumping, but that the overall time of carrying out the method would be substantially increased.

Pre-heating of the water may further control gas evolution. The water is pre-heated as opening 90 in the inlet tube directs the water against connector tube inner wall surface 96, and the water flows down the inner wall into vessel 22.

After the dilution step is finished, the scrubber and blower are turned off, the reaction vessel is removed from the microwave system, and the digestate is analyzed.

A particularly suitable material for the reaction vessel is borosilicate glass or quartz glass. Compared to a borosilicate glass vessel, a quartz vessel advantageously is more microwave transparent, thereby providing a relatively shorter digestion time, the power output being constant. Furthermore, a quartz vessel withstands thermal shock better. Moreover, with a sample containing more than about 30% protein, especially 45% or more protein, a quartz vessel surprisingly yields more accurate results.

Alternatively, scrubber 120 may be off until the beginning of the second heating stage, and furthermore when turned on, may be regulated to provide a negative pressure less than the positive pressure generated by the off gases. This variation permits positive pressure build up and causes an overall positive pressure to be maintained upstream from trap 124, thereby making boil-over even more unlikely. With this modification, valve 122 remains closed until a negative pressure is produced within the reaction vessel during the dilution step.

In the Example that follows and throughout this description and the claims set forth below, all percentages are by weight/weight, and all procedures are carried out at ambient temperature and pressure, unless otherwise specified.

EXAMPLE

A 1.0 g sample of meat is weighed out on a 24×40 microslide cover glass and dropped through a 29/42 ground glass joint of the neck of quartz, flat bottom, boiling flask 22 (500 ml). 10 ml of concentrated sulfuric acid, 0.75 g of mercuric oxide and 15 g of potassium sulfate are added to the flask.

Lower portion 28 of the flask is insulated by a molded, glass fiber cup 30 having a thickness of 4.5 mm +/− 1 mm. The insulated flask is placed in internal chamber 16 of microwave 12, flask mouth 25 is sealingly mated to rounded joint 46 of the connector tube, and the microwave door is closed.

With scrubber 120 and blower 126 turned on, approximately 2.5 ml of 40% hydrogen peroxide is injected into the reaction flask. Thereafter, digestion is immediately begun by the application of microwave energy to the flask contents. A first heating stage in which 100% power output is used for 1.75 minutes, is followed by a second heating stage in which 70% power is applied for 2.5 minutes.

Immediately after the second heating stage, about 90 ml of water is added to the flask using a pulsed addition involving seventy pulses in each of which the water input line is open for about 0.3 seconds and closed for about 0.65 seconds, with the water line being open thereafter for about 40 seconds.

The scrubber and blower are turned off, the reaction flask is removed from the microwave, and the digestate is analyzed for percent protein.

The above example is illustrative of the present invention. It is to be understood that the example is not in any way to be interpreted as limiting the scope of the invention. Rather, it is intended that the scope of the invention be defined by the claims set forth below. It is contemplated that the invention as hereinafter claimed, will be subject to various modifications within the scope thereof.

Industrial Applicability

The microwave-based apparatus of the present invention is useful for rapid sample digestion.

We claim:

1. Microwave-based apparatus useful for digestion, comprising
   (a) a microwave system having a wall with means defining an aperture formed therethrough, said microwave system comprising an internal chamber formed in part by an interior surface of said wall;
   (b) a reaction vessel disposed within said internal chamber, a portion of said reaction vessel being insulated;
   (c) a connector tube slidably disposed in said aperture of said wall, said connector tube having a portion exterior to said internal chamber and a portion that extends into said internal chamber, an end of said slidably disposed connector tube being joined to a mouth of said reaction vessel by biasing means located outside said internal chamber; and
   (d) external suction means connected to said connector tube.

2. The digestion apparatus of claim 1, further comprising means for providing pulsed addition of a liquid to said reaction vessel.

3. The digestion apparatus of claim 1, wherein said means for biasing are springs.

4. The digestion apparatus of claim 1, wherein said connector tube is vertically disposed.

5. The digestion apparatus of claim 1, wherein said biasing means is attached to said wall of said microwave system and to the portion of said connector tube exterior to said internal chamber.

6. The digestion apparatus of claim 1, wherein said insulated portion of said reaction vessel is a lower portion.

7. The digestion apparatus of claim 1, wherein said connector tube comprises tube means coaxially disposed within said connector tube.

8. The digestion apparatus of claim 7, wherein a side wall of a delivery end of said tube means includes an opening for fluid delivery.

9. The digestion apparatus of claim 1, wherein said reaction vessel is made of quartz glass.

10. The digestion apparatus of claim 1, wherein glass fiber insulation is used.

* * * * *